(12) United States Patent
Cavazza

(10) Patent No.: US 6,602,512 B1
(45) Date of Patent: Aug. 5, 2003

(54) COMPOSITION FOR THE PREVENTION OF MUSCLE FATIQUE AND SKELETAL MUSCLE ADAPTATION OF STRENUOUS EXERCISE

(75) Inventor: Claudio Cavazza, Rome (IT)

(73) Assignee: Sigma-Tau HealthScience S.p.A., Pomezia (IT)

( * ) Notice: Subject to any disclaimer, the term of this patent is extended or adjusted under 35 U.S.C. 154(b) by 0 days.

(21) Appl. No.: 10/019,546

(22) PCT Filed: Jul. 21, 2000

(86) PCT No.: PCT/IT00/00308

§ 371 (c)(1),
(2), (4) Date: Jan. 3, 2002

(87) PCT Pub. No.: WO01/06873

PCT Pub. Date: Feb. 1, 2001

(30) Foreign Application Priority Data

Jul. 23, 1999 (IT) ......................................... RM99A0467

(51) Int. Cl.⁷ ................................................ A61K 9/00
(52) U.S. Cl. ........................ 424/400; 424/725; 514/23; 514/168
(58) Field of Search ................. 424/439, 400, 424/725; 514/23, 168; 435/8

(56) References Cited

U.S. PATENT DOCUMENTS

| 4,194,006 A | * | 3/1980 | Cavazza |
| 4,376,117 A |   | 3/1983 | Godfraind et al. |
| 6,080,788 A | * | 6/2000 | Sole et al. |

FOREIGN PATENT DOCUMENTS

| WO | 98 43499 A    |   | 10/1998 |
| WO | WO 99/03365   | * | 1/1999  |
| WO | 99 51097 A    |   | 10/1999 |
| WO | 00 43022 A    |   | 7/2000  |

OTHER PUBLICATIONS

Database CHEMABS 'Online!; Chemical Abstracts Service, Columbus, Ohio, US; 1976; Ferrini R et al.: "Action of creatinol; 0-phosphate on isolated rabbit atria and the rat phrenic nerve—diaphragm preparation" Database accession No. 1976:25819 ZCAPLUS; XP002152051; abstract & II Farmaco, vol. 30, No. 11, 1975, pp. 912–916, XP000960318; Rome, IT; p. 915, column CONCL.–p. 916, paragraph 1; figure 2 Abstract Only RN).

Database CHEMABS 'Online!; Chemical Abstracts Service, Columbus, Ohio, US; Marzo A et al.: "Pharmacokinetics of creatinol 0–phophate"; Database accession No. 1973:80 ZCAPLUS; XP002152052; abstract & Clinica Terapeutica., vol. 62, No. 5, 1972, pp. 419–430, Societa Editrice Universo, Rome., IT; ISSN: 0009–9074 Abstract Only.

Budavari et.al.: "The Merck Index"; 1991, Merck & Co., Inc. ,Raway, N.J.,; U.S.A XP002151820 p. 1166, paragraph 7315.

Packer L et al:"Free Radical Scavenging is Involved in the Protective Effect of L–Propionyl–Carnitine Against Ischemia–Reperfusion Injury of the Heart" Archives of Biochemistry and Biophysics,US,New York, US, vol. 288, No. 2, Aug. 1, 1991, pp. 533–537, XP000654050; ISSN:0003–9861 p. 534, right–hand column –p. 535, left–hand column.

* cited by examiner

Primary Examiner—Leon B. Lankford, Jr.
Assistant Examiner—Ruth A. Davis
(74) Attorney, Agent, or Firm—Nixon & Vanderhye P.C.

(57) ABSTRACT

A composition is disclosed suitable for the prevention and/or treatment of muscular energetic deficiencies and states of asthenia for enhancing sport performances and for the treatment of states of heart fatigue, that may take the form of a dietary supplement, dietetic support or of an actual medicine, which comprises as characterizing active ingredients a combination of L-carnitine and/or at least one alkanoyl L-carnitine and creatinol-phosphate.

7 Claims, No Drawings

COMPOSITION FOR THE PREVENTION OF MUSCLE FATIQUE AND SKELETAL MUSCLE ADAPTATION OF STRENUOUS EXERCISE

This application is the U.S. national phase of international application PCT/IT00/00308 filed Jul. 21, 2000, which designated the U.S.

The present invention relates to a composition for the prevention and treatment of muscular energetic deficiencies, states of asthenia and muscle fatigue, states of heart fatigue and post-infarct conditions and for enhancing sporting performances.

Accordingly, the composition may take the form and exert the action of a dietary supplement or of an actual medicine, depending upon the support or preventive action, or the strictly therapeutic action, which the composition is intended to exert in relation to the particular individuals it is to be used in.

More particularly the present invention relates to a n orally, parenterally, rectally or transdermally administrable combination composition which comprises as characterizing ingredients:
- (a) at least on e carnitine s elected from the group consisting of L-carnitine, acetyl L-carnitine, propionyl L-carnitine, butyryl L-carnitine, valeryl L-carnitine and isovaleryl L-carnitine or a pharmacologically acceptable salt thereof, and
- (b) creatinol-phosphate or a pharmacologically acceptable salt thereof.

Compositions comprising carnitines and creatine or phosphocreatine are already known. WO 98/43499 (Sigma-Tau) discloses a nutritional supplement for facilitating the adaptation of skeletal muscle in individuals undergoing programs of strenuous exercise and counteracting defatigation and weariness in asthenic individuals, which comprises a combination of L-carnitine, acetyl L-carnitine and propionyl L-carnitine as basic active ingredients which may also comprise creatine and/or phosphocreatine as optionally additive components.

U.S. Pat. No. 4,376,117 (Simes) discloses the magnesium salt of creatinol-O-phosphate which is useful in the treatment and prevention of myocardiac infarction.

Both carnitine and creatinol-phosphate [1-(2-hydroxyethyl)-1-methylguanidine-O-phosphate] are well known for their important metabolic and pharmacological effects which have led to several positive pharmacological and clinical findings.

The carnitines are known to play a major role in the processes of beta-oxidation of fatty acids in the formation of ATP. They are also endowed with important antioxidant activity as demonstrated by their protective effect on lipid peroxidation of the cellular phospholipid membranes and on oxidative stress induced at the myocardial and endothelial cells level. These biochemical effects of the carnitines are reflected by the favourable results obtained in clinical practice with their use in the treatment of various forms of atherosclerosis. myocardial ischaemia, peripheral vasculopaties and diabete.

Creatinol-phosphate, which is a compound structurally akin to creatine phosphate, from which it differs in its greater stability and in various metabolic and pharmacodynamic aspects, belongs to that group of phosphagens which play a fundamental role in muscle energy processes. It is known, in fact, that creatine phosphate is strongly involved in the processes responsible, in muscles, for ATP synthesis which is reduced during muscular exercise.

Creatine, creatine phosphate, creatine phosphokinase, ATP and ADP are fundamental biochemical structures responsible for muscle function, particularly in anaerobic conditions. However, creatine, above all others, is the essential compound conditioning the remaining steps, its presence being of fundamental importance for achieving phosphorylation and the associated ATP-related energy processes. Its administration leads, in fact, to an increase in its muscular concentration and to an increase in creatine phosphate.

To obtain these effects in human subjects, however, the administration of high doses of creatine is necessary, up to and beyond 20 g per day, with consequent adverse side effects, particularly at the renal level. Even though only approximately a quarter of the creatine administered can be transformed into creatine phosphate, administration of the latter is not a practical proposition on account of its instability and the difficulty of oral administration. It would, therefore, appear to be of great interest to provide another phosphorous-bearing derivative belonging to the pool of organic phosphates which is endowed with great stability and excellent tolerability and can also be administered orally, such as creatinol-phosphate, the administration of which, even at low doses, induces a substantial increase in muscular creatine and the consequent formation of creatine phosphate. Its administration causes an increase in muscular strength in human subjects, which is also marked in the elderly, as well as the disappearance of asthenia and muscular weakness in convalescent subjects and the restoration of cardiac efficiency in subjects who have suffered an infarct.

Potentially even more interesting, however, also with a view to its action on muscular activity, are the results of experiments indicating its ability to stabilise the cell membranes which may be more resistant to attack by reactive oxygen species (ROS).

Since, as is known, one of the effects that forced muscular exercise may induce at muscle level are lesions of the muscle fibres themselves related to oxygen toxicity and to the products of lipid peroxidation, one of the favourable effects of creatinol-phosphate consists in its ability to protect the musculature against ROS-induced lesions.

It has now surprisingly been found that a combination composition comprising as its characterising components:
- (a) at least one carnitine selected from the group consisting of L-carnitine, acetyl L-carnitine, propionyl L-carnitine, butyryl L-carnitine, valeryl L-carnitine and isovaleryl L-carnitine or a pharmacologically acceptable salt thereof, and
- (b) creatinol-phosphate or its pharmacologically acceptable salt, is extremely effective for the prevention and treatment of muscular energy deficiencies, states of asthenia and muscle fatigue, states of heart fatigue and postinfarct conditions, and for enhancing sporting performance, owing to the potent, unexpected synergistic effect exerted by its components.

Toxicology Tests

Both the carnitines and creatinol-phosphate are products known for their low toxicity and good tolerability.

In tests performed in rats, doses of L-carnitine and creatinol-phosphate in combination, corresponding to 250 mg/kg of each compound, were administered intraperitoneally without the occurrence of any signs of toxicity. Likewise, no signs of toxicity were detected when 750 mg/kg of L-carnitine were administered orally in combination with 750 mg/kg of creatinol-phosphate. Even prolonged oral administration for one month of 200 mg/kg of L-carnitine plus 200 mg/kg of creatinol-phosphate to rats did not cause any toxic intolerance reaction. Full blood counts and blood-chemistry tests performed at the end of treatment also failed to reveal any abnormalities worthy of note as compared to controls. At autopsy, none of the main organs showed any signs of distress. Histological and histochemical investigations confirmed these findings, the results being comparable to those obtained in the control animals.

Muscle Fatigue Test

The method described by Zheng (Zheng R. L., Acta Pharmacol. Sinica, 14, 47, 1993) was used for this test in order to observe whether the administration of L-carnitine or creatinol-phosphate or of the two products in combination might increase reaction time in treated animals as compared to controls.

In this test, different groups of mice received daily oral doses of 200 mg/kg of L-carnitine or 200 mg/kg of creatinol-phosphate or of the two compounds in combination over the 6-day period preceding the test. The animals were immersed in a tank full of water and swimming endurance time was measured.

Both L-carnitine and creatinol-phosphate increased swimming endurance time, but the greatest effect was observed in mice treated with the L-carnitine plus creatinol-phosphate combination. In these latter animals, in fact, swimming endurance time was significantly longer compared to controls, thus confirming the synergistic effect exerted by the components of the composition (see Table 1).

TABLE 1

Muscle fatigue test

| Treatment | Swimming time (min) |
| --- | --- |
| Controls | 93 ± 8 |
| L-carnitine | 118 ± 14 |
| Creatinol-phosphate | 124 ± 11 |
| L-carnitine + creatinol-phosphate | 191 ± 19 |

Forced Muscular Exercise Test

As is known, forced muscular exercise can produce structural and inflammatory-type lesions at muscle fibre level, due to the increased oxygen consumption and to production of reactive oxygen species (ROS). A marker of the level of ROS-induced lipid peroxidation of the muscle may be obtained from its malondialdehyde (MDA) concentration. For this test, the method described by Husain was used (Husain K., Pathophysiology, 4, 69, 1997) as modified by Li (Li J.X., Acta Pharmacologica Sinica, 20, 126, 1999) which consists essentially in examining rats on a treadmill at controlled belt speed and preset inclination. In this way the rats were made to run at a belt speed of 28 m/min and an inclination of approximately 5°. Exhaustion of the control animals subjected to the exercise occurred after approximately 90 minutes.

The test was performed on rats receiving daily oral treament over the 6-day period preceding the test with 200 mg/kg of L-carnitine or with 200 mg/kg of creatinol-phosphate or with the two compounds in combination.

Five minutes and 30 minutes, respectively, after the end of the test, the animals were sacrificed and samples of gastrocnemius muscle were taken for measurement of the malondialdehyde (MDA) content using the reaction with thiobarbituric acid according to the method described by Ohkawa (Ohkawa H. Angl. Biochem 95, 351, 1979).

The results of this test are illustrated in Table 2, which show that the combination of L-carnitine plus creatinol-phosphate induces a highly significant and unexpected reduction in the MDA concentration present in the muscle samples. This demonstrates the unexpected synergistic effect of L-carnitine and creatinol-phosphate in protecting muscle against damages induced by the reactive oxygen species (ROS) produced in the course of forced muscular exercise.

TABLE 2

Forced muscular exercise test

| | MDA content in muscle (nmol.g$^{-1}$) | |
| --- | --- | --- |
| Treatment | After 5 min | After 30 min |
| Controls | 240 ± 4 | 236 ± 10 |
| L-carnitine | 218 ± 11 | 216 ± 14 |
| Creatinol-phosphate | 206 ± 16 | 209 ± 12 |
| L-carnitine + creatinol-phosphate | 163 ± 14 | 169 ± 19 |

Tests of ATP Content in Rabbit Papillary Muscle after Hypoxia

By submitting sections of rabbit papillary muscle to hypoxia a reduction in muscular ATP content can be induced. The presence in perfusion fluid of substances which interact in muscular energy metabolism may limit the hypoxia-induced loss of ATP content in muscle.

For this test a group of New Zealand rabbits were used. The rabbits received intravenous administrations of 100 mg/kg of L-carnitine or 100 mg/kg of creatinol-phosphate or the two compounds in combination every day over the 3-day period preceding the test. After the third day of treatment, all animals, including control animals, were sacrificed.

After removing the hearts, sections of papillary muscle measuring 1 mm in diameter and 4-5 cm in thickness were isolated. These tissue sections were perfused in a thermostatic bath with a 100% $O_2$-saturated solution. On introducing 100% $N_2$ into the bath instead of the $O_2$, hypoxia was induced and maintained for the duration of 90 minutes. The tissues were then maintained in conditions of normal perfusion for a further period of 90 minutes. The ATP content of the papillary muscle was estimated according to the method described by Strehler (Strehler B.L., Methods in Enzymology III, N.Y. Acad. Press, 871, 1957.

The results of this test are presented in Table 3, which shows that the combination of L-carnitine plus creatinol-phosphate unexpectedly affords a surprisingly greater degree of protection against the ATP reduction in papillary muscle subjected to hypoxia than does L-carnitine and creatinol-phosphate alone, thus demonstrating the synergistic effect of the two compounds present in the composition.

TABLE 3

Test of ATP content of rabbit papillary muscle

| | ATP concentration (mol/g tissue) | |
| --- | --- | --- |
| Treatment | Before hypoxia | After hypoxia |
| Controls | 1.49 ± 0.29 | 0.39 ± 0.046 |
| L-carnitine | 1.53 ± 0.15 | 0.48 ± 0.036 |

TABLE 3-continued

Test of ATP content of rabbit papillary muscle

| Treatment | ATP concentration (mol/g tissue) | |
|---|---|---|
| | Before hypoxia | After hypoxia |
| Creatinol-phosphate | 1.55 ± 0.31 | 0.68 ± 0.045 |
| L-carnitine + creatinol-phosphate | 1.60 ± 0.28 | 1.18 ± 0.051 |

Illustrative, non-limiting examples of compositions according to the invention are reported hereinbelow.

| | | |
|---|---|---|
| 1) | L-carnitine | 400 mg |
| | Creatinol-phosphate | 400 mg |
| 2) | Acetyl L-carnitine | 300 mg |
| | Creatinol-phosphate | 800 mg |
| 3) | Carnitine mixture | 300 mg |
| | (L-carnitine 100 mg, acetyl L-carnitine 100 mg, propionyl L-carnitine 100 mg) | |
| | Creatinol-phosphate | 300 mg |
| 4) | L-carnitine | 200 mg |
| | Creatinol-phosphate | 200 mg |
| | Creatine | 100 mg |
| | Taurine | 50 mg |
| | Inosine | 50 mg |
| | Coenzyme $Q_{10}$ | 25 mg |
| | Selenium methionine | 50 µg |
| | Vitamin E | 5 mg |
| | Beta-carotene | 5 mg |
| 5) | L-carnitine | 100 mg |
| | Creatinol-phosphate | 100 mg |
| | Phosphocreatinine | 100 mg |
| | Creatine | 100 mg |
| | Inosine | 100 mg |
| | Vitamin C | 50 mg |
| | Vitamin E | 5 mg |
| | Beta-carotene | 5 mg |
| | Coenzyme $Q_{10}$ | 25 mg |
| 6) | L-carnitine | 200 mg |
| | Creatinol-phosphate | 200 mg |
| | Fructose-1,6-diphosphate | 200 mg |
| | Maltodextrin | 200 mg |
| | Magnesium | 10 mg |
| | Selenium methionine | 50 µg |
| | Zinc | 10 mg |
| | Manganese | 1 mg |
| | Coenzyme $Q_{10}$ | 25 mg |
| 7) | L-carnitine | 500 mg |
| | Creatinol-phosphate | 500 mg |
| | Creatine | 500 mg |
| | Coenzyme $Q_{10}$ | 50 mg |
| | Vitamin E | 10 mg |
| | Vitamin C | 100 mg |
| | Beta-carotene | 5 mg |
| | Magnesium | 10 mg |

What is meant by pharmacologically acceptable salt of L-carnitine or alkanoyl L-carnitine is any salt of these active ingredients with an acid that does not give rise to unwanted toxic or side effects. Such salts are well known to pharmacy experts.

Examples of suitable salts, though not exclusively these, are: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in Int. J. of Pharm. 33, (1986), 201–217; this publication is incorporated herein by reference.

What is claimed is:

1. An orally, parenterally, rectally or transdermally administrable combination composition which comprises the following components:

(a) at least one carnitine selected from the group consisting of L-carnitine, acetyl L-carnitine, propionyl L-carnitine, butyryl L-carnitine, valeryl L-carnitine and isovaleryl L-carnitine or a pharmacologically acceptable salt thereof, and (b) 1-(2-hydroxyethyl)-1-methylguanidine-O-phosphate or a pharmacologically acceptable salt thereof.

2. The composition of claim 1, wherein the weight ratio (a):(b) is from 1:0.1 to 1:1.

3. The composition of claim 1, wherein the pharmacologically acceptable salt of component (a) is selected from the group consisting of: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; orotate; acid oxalate; sulphate, acid sulphate; trichloroacetate; trifiporoacetate and methane sulphonate.

4. The composition of claim 1, which further comprises vitamins, coenzymes, mineral substances, antioxidants, sugars, aminoacids and proteins.

5. A method of preventing or treating muscular energetic deficiencies, asthenia, muscle fatigue, heart fatigue, post-infarct heart conditions or enhancing sporting performances, said method comprising orally, parenterally, rectally or transdermally administering a combination comprising the following components:

(a) at least one carnitine selected from the group consisting of L-carnitine, acetyl L-carnitine, propionyl L-carnitine, butyryl L-carnitine, valeryl L-carnitine and isovaleryl L-carnitine or a pharmacologically acceptable salt thereof, and (b) 1-(2-hydroxyethyl)-1-methylguanidine-O-phosphate or a pharmacologically acceptable salt thereof.

6. The method of claim 5, wherein the weight ratio (a):(b) is from 1:0.1 to 1:1.

7. The method of claim 5, wherein the pharmacologically acceptable salt of component (a) is selected from the group consisting of: chloride; bromide; iodide; an, aspartate, acid aspartate; citrate, acid citrate; tartrate; phosphate, acid phosphate; fumarate, acid fumarate; glycerophosphate; glucose phosphate; lactate; maleate, acid maleate; orotate; acid oxalate; sulphate, acid sulphate; trichioroacetate; trifiporoacetate and methane sulphonate.

* * * * *